United States Patent [19]

Elder et al.

[11] Patent Number: 4,610,166
[45] Date of Patent: Sep. 9, 1986

[54] METHOD AND APPARATUS FOR TESTING WELDS IN PLASTIC PIPE

[75] Inventors: Charles D. Elder; Thomas E. Reder, both of Midland, Mich.

[73] Assignee: The Dow Chemical Company, Midland, Mich.

[21] Appl. No.: 732,015

[22] Filed: May 6, 1985

[51] Int. Cl.⁴ .............................................. G01N 3/08
[52] U.S. Cl. ..................................................... 73/818

[58] Field of Search .................. 73/818, 825, 850, 860

[56] References Cited

U.S. PATENT DOCUMENTS 2,628,496  2/1953  Wick ..................................... 73/818

Primary Examiner—Anthony V. Ciarlante

[57] ABSTRACT

Welds in plastic pipe are tested by compressing the welded portion in a generally radial direction.

7 Claims, 4 Drawing Figures

METHOD AND APPARATUS FOR TESTING WELDS IN PLASTIC PIPE

For many applications it has been found to be desirable to utilize synthetic resinous piping. Such piping is employed with benefit in applications where relatively low operating pressures are encountered and is especially desirable where material such as aqueous solutions or waste water is employed which tends to corrode water pipe. Such synthetic resinous thermoplastic piping such as polyethylene pipe is often joined by welding. One particularly convenient method of welding such pipe employs an apparatus which fuses two facing adjacent pipe ends. A heated platen is placed between facing pipe ends, the pipe ends forced against the heated platen to heat plastify the adjacent pipe ends; the platen is removed and the heat plastified pipe ends placed in abutting engagement. On cooling, desirably, the pipe ends are welded together in a concentric relationship, the weld forming both an internal and an external bead. When such welding is done correctly, the strength of the weld exceeds that of the pipe wall. The quality of such a weld generally cannot be judged by the external appearance thereof. Frequently in defective welds cracks occur which terminate on the inner surface of the pipe and cannot be detected by external visual inspection.

It would be desirable if there were available an improved method and apparatus for the testing of welds formed in synthetic resinous thermoplastic pipe whether the welds be made by machine or hot gas and rod.

It would be desirable if such a method and apparatus were readily portable and suitable for field use.

It would also be desirable if such a method and apparatus provided means for nondestructive testing.

These features and other advantages are achieved in a method for the testing of welds in synthetic resinous thermoplastic flexible pipe, the steps of the method comprising applying radial compressive force in the region of a weld between two pipe sections to deform the welded portion of the pipe sections into a generally oval configuration, subsequently removing a deforming force from the welded pipe sections, subsequently applying a deforming force radially to the welded pipe sections in the region of the weld to return the pipe sections to a generally circular configuration.

Also contemplated within the scope of the present invention is a synthetic resinous thermoplastic pipe testing apparatus, the apparatus comprising a generally U-shaped frame, the frame having a first leg and a second leg and a base; a hydraulic cylinder affixed to the base, the hydraulic cylinder having a piston rod extending between and generally parallel the arms of the U-shaped frame, the piston rod being selectively positionable in a direction generally parallel the arms of the U; the piston rod having a pipe engaging member affixed thereto remote from the cylinder, the weld engaging member having a first pipe engaging face of generally planar configuration, the first pipe engaging face being generally normal to the direction of travel of the piston rod, the first pipe engaging member lying generally in the plane of the U-shaped frame; an anvil member extending between the legs of the U at a location remote from the base of the U and the hydraulic cylinder, the anvil member being releasably affixed to the legs of the U, the anvil member having affixed thereto a second pipe engaging member having a second pipe engaging face of generally like configuration to the first pipe engaging face, the pipe engaging faces being opposed and parallel.

Further features and advantages of the present invention will become more apparent from the following specification taken in connection with the drawing wherein.

Figure 1:
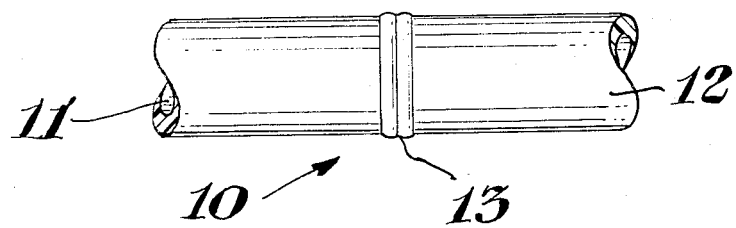
FIG. 1 is a schematic representation of a welded synthetic resinous thermoplastic pipe weld.

In FIG. 1 there is depicted a fractional view of a piping section generally designated by the reference numeral 10. The piping section 10 comprises a first pipe member 11 and a second pipe member 12. The members 11 and 12 are coaxially arranged and define therebetween a weld 13.

Figure 2:
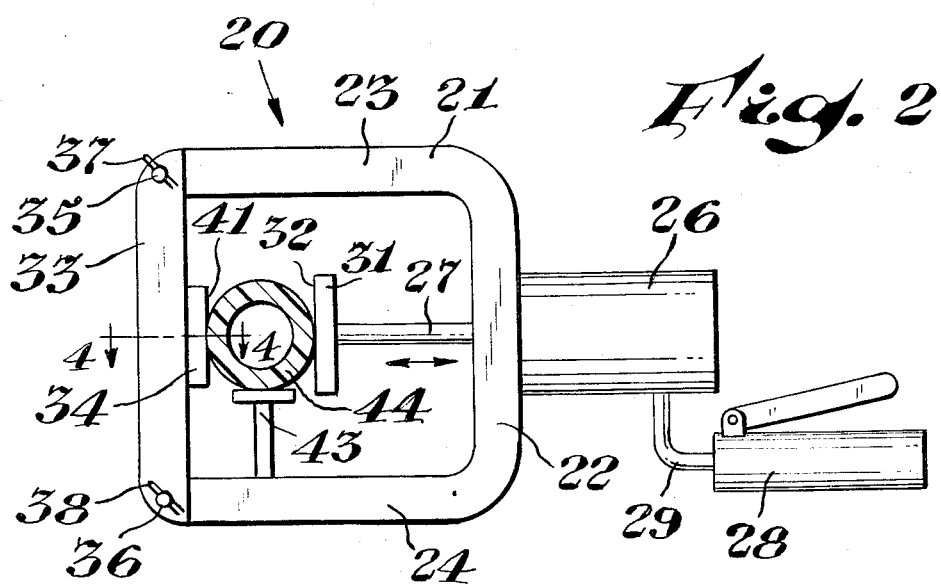
FIG. 2 is a side view of an apparatus in accordance with the present invention.

In FIG. 2 there is schematically depicted a side view of a weld testing apparatus in accordance with the present invention generally designated by the reference numeral 20. The apparatus 20 comprises in cooperative combination a generally U-shaped frame member 21. The frame member 21 comprises a base 22, a first leg 23 and a second leg 24. Affixed to the base 22 of the frame 21 is a hydraulic cylinder 26. The hydraulic cylinder 26 has a piston rod 27 which extends between and is generally parallel to the legs 23 and 24 and is capable of motion generally parallel thereto as indicated by the double headed arrow. The hydrualic cylinder 26 and piston rod 27 are actuated by means of a manually operated hydraulic pump 28 in communication with the cylinder by means of conduit 29. A weld engaging member 31 is affixed to the piston rod 27 at a location remote from cylinder 26. The weld engaging member 31 has a generally planar pipe engaging face 32 disposed remote from the cylinder 26 and facing ends of the legs 23 and 24 remote from the base 22. An anvil member 33 is detachably secured to the legs 23 and 24 at a location remote from the base 22 and hydraulic cylinder 26. The anvil member 33 is affixed to the legs 23 and 24 by means of hitch pins 35 and 36 which are secured by cotter pins 37 and 38. The anvil member 33 has affixed thereto a pipe engaging member 34 of generally similar configuration to the pipe engaging member 31. The pipe engaging member 34 has a pipe engaging face 41 parallel to and opposed to the face 32 of the pipe engaging member 31. As depicted in FIG. 1 there is shown a first pipe support means 43. Disposed between the faces 32 and 41 is a welded plastic pipe 44.

Figure 3:
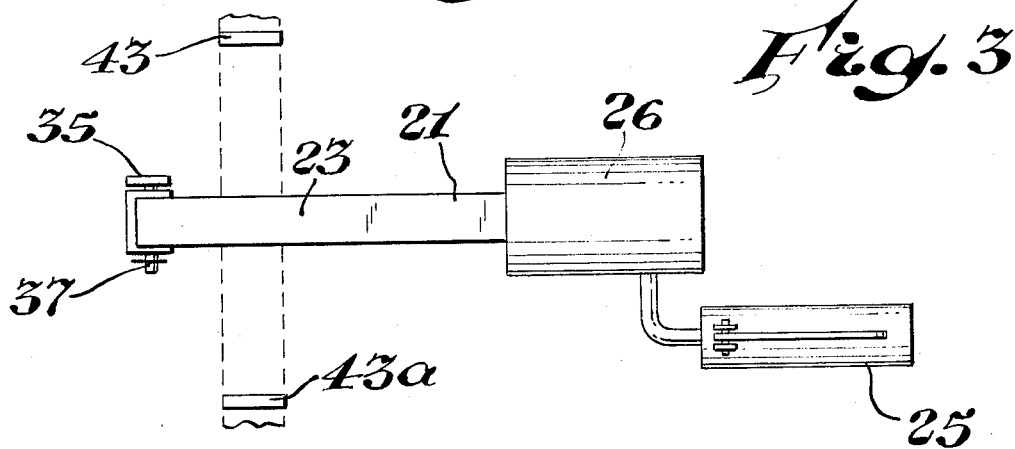
FIG. 3 is a top view of the apparatus of FIG. 2.

FIG. 3 shows a schematic top view of the apparatus of FIG. 1 wherein the location of pipe supports 43 and 43a are shown relative to the frame 21 of the location of the pipe indicated by dotted lines.

Figure 4:
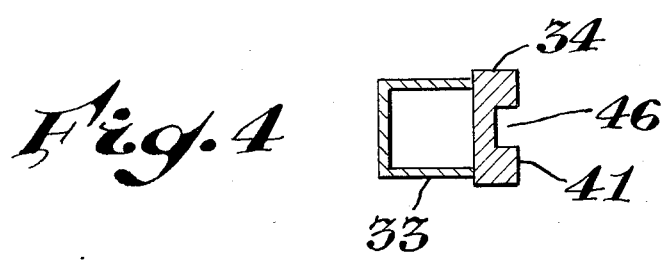
FIG. 4 is a schematic sectional view of the apparatus along the line 4—4 wherein the plastic pipe has been omitted.

FIG. 4 is a cross section view of the anvil 33 and the pipe engaging member 34 showing face 41 and a weld engaging recess 46.

In operation of the apparatus and in the practice of the method of the present invention, a pipe to be tested is positioned within the apparatus as depicted in FIG. 2 where advantageously the weld bead is received in a groove such as the groove 46. The pump 28 is actuated to radially compress the welded pipe section such as an ethylene polymer pipe in a radial direction to a desired degree depending upon the particular synthetic resinous thermoplastic material used. For example, on employing pipe made of high density polyethylene having a molecular weight of about 500,000 molecular weight units, compression to about 50 percent of the conduit's original inside diameter provides an adequately severe test. However, such polyethylene welded conduit, if the weld is good, can be compressed until the inner surface of the pipe contacts. Such compression of the pipe generally results in non-recoverable deformation. However, by rotating the pipe and apparatus 90 degrees relative to one another, the generally elliptical configuration of the pipe can be squeezed in a directional generally parallel to the major axis of the elliptical cross section and the conduit returned to a generally circular configuration. When defective welds are encountered, they provide audible evidence of the defect. The sounds range from a gentle cracking sound to a noise comparable to the discharge of a 38 caliber pistol. In some instances with defective welds a visible break can be observed.

In the event synthetic resinous thermoplastic pipes are to be tested which are more brittle than polyethylene, a section of unwelded pipe is deformed in the apparatus until ruptured, and one-half of such deformation can be employed for weld testing of such pipe.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A method for the testing of welds in synthetic resinous thermoplastic flexible pipe, the steps of the method comprising applying radial compressive force in the region of a weld between two pipe sections by using a recessed deforming member in contact with the pipe sections to deform the welded portion of the pipe sections into a generally oval configuration, detecting while applying radial compressive force, evidence of a defective weld, subsequently removing a deforming force from the welded pipe sections.

2. The method of claim 1 wherein the pipe sections in the region of the weld are deformed to give a reduction in inner diamater in the direction of compression of up to about 50 percent.

3. The method of claim 1 wherein the pipe is of an ethylene polymer.

4. The method of claim 3 wherein the pipe is polyethylene.

5. A synthetic resinous thermoplastic pipe testing apparatus, the apparatus comprising a generally U-shaped frame, the frame having a first leg and a second leg and a base; a hydraulic cylinder affixed to the base, the hydraulic cylinder having a piston rod extending between and generally parallel the arms of the U-shaped frame, the piston rod being selectively positionable in a direction generally parallel the arms of the U; the piston rod having a pipe engaging member affixed thereto remote from the cylinder, the weld engaging member having a first pipe engaging face of generally planar configuration, the first pipe engaging face being generally normal to the direction of travel of the piston rod; the first pipe engaging member lying generally in the plane of the U-shaped frame; an anvil member extending between the legs of the U at a location remote from the base of the U and the hydraulic cylinder, the anvil member being releasably affixed to the legs of the U, the anvil member having affixed thereto a second pipe engaging member having a second pipe engaging face of generally like configuration to the first pipe engaging face, the pipe engaging faces being opposed and parallel and having a recess.

6. The apparatus of claim 5 including a hydraulic pump in operative combination with a hydraulic cylinder.

7. The apparatus of claim 6 wherein the hydraulic pump is a manually operated hydraulic pump.

* * * * *